United States Patent
Hvid et al.

(10) Patent No.: US 11,534,325 B2
(45) Date of Patent: *Dec. 27, 2022

(54) METHOD FOR ANAL OR STOMAL IRRIGATION

(71) Applicant: Coloplast A/S, Humlebaek (DK)

(72) Inventors: Niels Hvid, Vedbaek (DK); Richard Morgan Hickmott, Helsingoer (DK); Rasmus Nielsen, Ringsted (DK); Luigi Ravasio, Monte Marenzo—LC (IT); David Ward, Milan (IT); Henrik Bay, Lyngby (DK)

(73) Assignee: Coloplast A/S, Humlebaek (DK)

( * ) Notice: Subject to any disclaimer, the term of this patent is extended or adjusted under 35 U.S.C. 154(b) by 211 days.

This patent is subject to a terminal disclaimer.

(21) Appl. No.: 17/004,000

(22) Filed: Aug. 27, 2020

(65) Prior Publication Data
US 2020/0390586 A1    Dec. 17, 2020

Related U.S. Application Data

(62) Division of application No. 15/536,674, filed as application No. PCT/DK2015/050403 on Dec. 17, 2015, now Pat. No. 10,792,184.

(30) Foreign Application Priority Data

Dec. 19, 2014  (DK) .......................... PA 2014 70807

(51) Int. Cl.
*A61F 5/442*  (2006.01)
*A61M 3/02*   (2006.01)

(52) U.S. Cl.
CPC ............. *A61F 5/442* (2013.01); *A61M 3/022* (2014.02); *A61M 3/0208* (2014.02); *A61M 3/0216* (2014.02); *A61M 3/0258* (2013.01); *A61M 3/0295* (2013.01); *A61M 3/0279* (2013.01); *A61M 2205/3331* (2013.01); *A61M 2205/3368* (2013.01); *A61M 2210/1064* (2013.01)

(58) Field of Classification Search
CPC ... A61F 5/442; A61M 3/0208; A61M 3/0216; A61M 3/022; A61M 3/0258; A61M 3/0295; A61M 3/0279
See application file for complete search history.

(56) References Cited

U.S. PATENT DOCUMENTS

| | | |
|---|---|---|
| 1,918,681 A | 7/1933 | Allen |
| 2,074,374 A | 3/1937 | Suarez De Mendoza |
| 2,157,756 A | 5/1939 | Irwin |
| 2,617,416 A * | 11/1952 | Condit .................. A61M 3/025 604/24 |
| 2,874,696 A | 2/1959 | Bried |
| 4,617,011 A | 10/1986 | Bloxom |

(Continued)

*Primary Examiner* — Guy K Townsend
(74) *Attorney, Agent, or Firm* — Coloplast Corp., Coloplast A/S; Nick Baumann

(57) ABSTRACT

A method for anal or stomal irrigation includes providing an irrigation system to a user and instructing the user to operate the system to expel the irrigating liquid from a catheter tip. The irrigation pressure is controlled with the control system in response to input from a sensor such that a pressure at the catheter tip approaches a predetermined threshold pressure value without exceeding the predetermined pressure value.

21 Claims, 7 Drawing Sheets

(56) References Cited

U.S. PATENT DOCUMENTS

| | | | | |
|---|---|---|---|---|
| 6,595,971 | B1* | 7/2003 | von Dyck | A61F 5/442 604/334 |
| 6,723,079 | B2* | 4/2004 | Cline | A61F 5/448 604/338 |
| 6,840,923 | B1* | 1/2005 | Lapcevic | A61M 3/0287 604/319 |
| 7,160,274 | B2 | 1/2007 | Ciok et al. | |
| 7,765,006 | B2* | 7/2010 | Martino | A61N 1/36007 607/40 |
| 7,765,007 | B2* | 7/2010 | Martino | A61N 1/36007 607/40 |
| 8,016,802 | B1* | 9/2011 | Schena | A61F 5/442 137/15.01 |
| 8,092,437 | B2* | 1/2012 | Cline | A61F 5/445 604/277 |
| 8,096,980 | B2* | 1/2012 | Cline | A61F 5/445 604/277 |
| 8,608,722 | B2 | 12/2013 | Luther | |
| 8,821,464 | B2* | 9/2014 | Hanuka | A61F 5/441 604/333 |
| 8,821,465 | B2* | 9/2014 | Hanuka | A61F 5/4407 604/333 |
| 8,845,607 | B2* | 9/2014 | Hanuka | A61F 5/443 604/333 |
| 8,858,519 | B2* | 10/2014 | Hanuka | A61F 5/4404 604/333 |
| 8,864,729 | B2* | 10/2014 | Hanuka | A61F 5/443 604/334 |
| 8,900,116 | B2* | 12/2014 | Hanuka | A61F 2/04 600/32 |
| 8,905,993 | B2 | 12/2014 | Luther | |
| 8,998,862 | B2* | 4/2015 | Hanuka | A61F 5/4405 604/318 |
| 8,998,867 | B2* | 4/2015 | Sabeti | A61F 5/4405 604/335 |
| 9,333,287 | B2 | 5/2016 | Nitsan et al. | |
| 9,610,220 | B2 | 4/2017 | Andersson et al. | |
| 9,919,093 | B2 | 3/2018 | Andreen et al. | |
| 9,968,728 | B2 | 5/2018 | Andersson | |
| 10,350,345 | B2 | 7/2019 | Andersson et al. | |
| 10,434,241 | B2 | 10/2019 | Hvid et al. | |
| 10,537,461 | B2* | 1/2020 | Hanuka | A61F 5/441 |
| 10,569,008 | B2 | 2/2020 | Andersson | |
| 10,569,009 | B2 | 2/2020 | Eliasson et al. | |
| 10,792,184 | B2* | 10/2020 | Hvid | A61M 3/0258 |
| 2003/0073963 | A1* | 4/2003 | Falconer | A61M 3/0262 604/328 |
| 2003/0073974 | A1* | 4/2003 | Falconer | A61M 3/0279 604/514 |
| 2003/0229324 | A1* | 12/2003 | King | A61M 3/0287 604/339 |
| 2004/0054339 | A1* | 3/2004 | Ciok | A61F 5/442 604/334 |
| 2005/0119628 | A1* | 6/2005 | Sant | A61M 3/0208 604/275 |
| 2006/0150310 | A1 | 7/2006 | Tsai | |
| 2006/0247604 | A1 | 11/2006 | Bruno | |
| 2006/0253090 | A1* | 11/2006 | Bradley | A61F 5/445 604/334 |
| 2008/0208172 | A1* | 8/2008 | Marshall | A61M 1/82 604/540 |
| 2010/0191264 | A1 | 7/2010 | Kassab et al. | |
| 2010/0204681 | A1 | 8/2010 | Luther | |
| 2011/0087197 | A1 | 4/2011 | Mombrinie et al. | |
| 2011/0092892 | A1 | 4/2011 | Nitsan et al. | |
| 2011/0196323 | A1* | 8/2011 | Gill | A61F 5/4405 604/333 |
| 2012/0289892 | A1 | 11/2012 | Shtul et al. | |
| 2013/0060213 | A1* | 3/2013 | Hanuka | A61F 5/441 604/344 |
| 2013/0066297 | A1* | 3/2013 | Shtul | A61M 3/0212 604/257 |
| 2013/0079736 | A1* | 3/2013 | Hanuka | A61F 5/4407 604/318 |
| 2013/0079737 | A1* | 3/2013 | Hanuka | A61F 5/449 604/318 |
| 2013/0079738 | A1* | 3/2013 | Hanuka | A61F 5/445 604/335 |
| 2013/0085442 | A1 | 4/2013 | Shtul et al. | |
| 2014/0005602 | A1* | 1/2014 | Andreen | A61M 3/0258 604/98.01 |
| 2014/0066853 | A1 | 3/2014 | Luther | |
| 2014/0155864 | A1 | 6/2014 | Andreen | |
| 2014/0296831 | A1 | 10/2014 | Goebel | |
| 2015/0025488 | A1* | 1/2015 | Hanuka | A61F 5/4405 604/335 |
| 2015/0335529 | A1* | 11/2015 | Andersson | A61M 3/0258 29/592 |
| 2016/0193403 | A1 | 7/2016 | Andersson | |
| 2016/0206805 | A1 | 7/2016 | Hassidov et al. | |
| 2017/0157314 | A1 | 6/2017 | Andersson et al. | |
| 2017/0340804 | A1 | 11/2017 | Hvid et al. | |
| 2017/0348137 | A1 | 12/2017 | Hvid et al. | |
| 2017/0348138 | A1 | 12/2017 | Hvid et al. | |
| 2018/0078700 | A1 | 3/2018 | Eliasson | |
| 2018/0177937 | A1 | 6/2018 | Eliasson et al. | |
| 2018/0256808 | A1 | 9/2018 | Andersson | |
| 2018/0311480 | A1 | 11/2018 | Goebel | |
| 2018/0311481 | A1 | 11/2018 | Goebel | |
| 2018/0369474 | A1 | 12/2018 | Falleboe et al. | |
| 2019/0192836 | A1 | 6/2019 | Goebel | |
| 2019/0358390 | A1 | 11/2019 | Goebel | |

\* cited by examiner

METHOD FOR ANAL OR STOMAL IRRIGATION

TECHNICAL FIELD

A system and a method for anal and/or stomal irrigation are provided, the system comprising a reservoir for an irrigating liquid, and a catheter comprising a catheter tip for insertion into the rectum and/or stoma of a user. In particular a pump and tubing system for controlling the supply of the irrigating liquid to the catheter tip and a control system for controlling operation of the pump are provided.

DETAILED DESCRIPTION

Control of voluntary bowel functions is frequently limited or absent in patients suffering from certain disabilities, such as spinal injuries, multiple sclerosis or spina bifida. Such lack of control of voluntary bowel functions typically results in faecal incontinence or intractable constipation, as patients have significantly reduced ability to sense the presence of faeces in the colon terminal part and the rectum and to sense the evacuation stimulus. Patients having undergone stomal surgery wherein a catheterizable stoma is constructed may suffer from similar difficulties.

It is known to accomplish bowel emptying by irrigation (i.e. flushing) of the rectum or stoma, by an irrigating fluid, such as tap water or saline, which is provided through an intermittent catheter with a tip which is configured and sized for insertion into the rectum or stoma, where it remains in a fixed position by an expandable inflation element, such as a balloon. The balloon may be inflatable by air or by water. Once the rectum or stoma has been flushed with the irrigating liquid, the expandable retention element is allowed to collapse to its non-deflated state, allowing the catheter to be withdrawn from the rectum or stoma, and allowing the liquid and faeces to evacuate. The catheter is connected to a reservoir of the irrigating liquid through a tube, and a pump may be provided for displacing the irrigating liquid from the reservoir to the catheter.

The development of transanal or transstomal irrigation systems has hitherto focussed on aspects of tubings, catheters and structural designs of pumps. It is hence an object to improve known systems further, in particular by improving control and user-convenience in relation to self-irrigation, and more particularly by improving control and operation of the pump. In particular, it is an object to detect the presence of irrigating liquid at the tip of the catheter and to accurately control dispensing of the irrigating liquid from the tip of the catheter.

SUMMARY

A system for anal and/or stomal irrigation is provided, said system comprising:
a reservoir for an irrigating liquid;
a catheter comprising a catheter tip for insertion into the rectum or stoma of a user and for expelling of the irrigating liquid from the catheter tip;
a tubing system providing a conduit for the irrigating liquid between the reservoir and the catheter tip;
a pump operable to pump the irrigating liquid from the reservoir to the catheter tip; and
a control system;
said control system being configured to control operation of the pump in response to a measure of pressure.

In a second aspect, a method for controlling a system for anal and/or stomal irrigation is provided, said system comprising:
a reservoir for an irrigating liquid;
a catheter comprising a catheter tip for insertion into the rectum or stoma of a user and for expelling of the irrigating liquid from the catheter tip;
a tubing system providing a conduit for the irrigating liquid between the reservoir and the catheter tip;
a pump operable to pump the irrigating liquid from the reservoir to the catheter tip; and
a control system;
said control system being configured to control operation of the pump in response to a measure of pressure,
said method comprising operating the control system to control the pumping operation of the pump in response to said measure of pressure.

The method may further comprise the step of determining the measure of pressure at a first predetermined position in the tubing system, in the pump, and/or in the catheter, before, during, or after operation of the pump.

The method may further comprise the step of determining or estimating a flow condition at the catheter tip on the basis of said measure of pressure.

The pumping operation of the pump may be increased or decreased in response to a measure of pressure. Most suitably, the pumping effect decreases in response to the measure of pressure. The pumping effect may decrease in a linear manner, or an asymptotic manner. An asymptotic decrease in the pumping operation of the pump allows the pressure at the tip of the catheter to gradually approach a predetermined threshold value (e.g. 2 psi) without exceeding it.

By decreasing the pressure at the tip of the catheter gradually, the user does not experience a sudden "cut-off" in the pumping operation, or an abrupt interruption in the liquid flow. User experience is thereby improved.

The measure of pressure could be indicative of a pressure at different locations in the system, e.g. in the pump, in the tubing system and/or in the catheter. The measure could be an electrical signal directly comparable with a specific pressure for a specific location, or it could be an electrical signal which is significant for an average pressure level in the system.

The control system may be configured, based on the measure of pressure, to determine or estimate a flow condition, e.g. at the catheter tip, in the tubing system, or in the pump.

In one example, the control system may be configured to determine when the tubing system and catheter is filled with—or emptied of—the irrigation liquid. The pump may run and detect when the transition from fluid pumping to air pumping (or vice-versa) occurs, by means of a change in resistance to the pump. This is referred to as priming, and it can be determined by the measure of pressure, or based on power consumption of the pump. This is—for example—carried out in order to remove air from the tubing system and to ensure filling of irrigation liquid. In one example, the control system may be configured to determine an amount of the irrigation liquid that leaves the system through the catheter. In another example, the control system may be configured to determine an amount of the irrigation liquid that is contained in the tubing system. In another example, the control system may be configured to determine an amount of the irrigation liquid that is flushed backwards due to leakage in the pump. Such a configuration would be able to compensate pump speed and ensure a more constant flow rate.

The pump comprises a motor-driven pump which is electronically controllable. The measure of pressure may be provided in different ways. In one embodiment, the measure is obtained from the characteristics of the power which is supplied to, and consumed by the pump. Herein, we refer to this signal as "the power signal". When the pressure changes, the motor which drives the pump will typically consume more or less power, or the voltage will increase or decrease. This changes the power signal which again may be used as a measure of pressure.

In particular, the control system may be configured to determine a measure of pressure from the power signal.

Alternatively, or in addition, the system may comprise one or more pressure sensors, e.g. located to determine a pressure. Such pressure sensors may be located at different predetermined locations. Particularly, a pressure sensor may be located in a first predetermined position. The first predetermined position could e.g. be in the tubing system or in the catheter. Additionally, another pressure sensor could be located at a second predetermined position. Again, this second predetermined position could be in the tubing system or in the catheter. The pressure determined by such a sensor or sensors is communicated to the control system and the pump could be controlled based thereon.

Accordingly, the measure of a pressure may include the measurements obtained by such sensors and/or measurements obtained by use of the power signal, or the measure of a pressure may be constituted by a measurement obtained by such sensors or from the power signal.

The measure of pressure may include several different pressure signals, e.g. obtained at different locations and/or obtained by different means and/or from different sensors.

If the predetermined position of the sensor is very close to the tip of the catheter, it is possible to obtain more correct measurements of the pressure at the tip and thereby a more exact measurement or estimation of the pressure when it leaves the catheter.

Particularly, vertical movement of the catheter will have less influence on the difference between the pressure measurements and the actual pressure at the tip when the distance between the predetermined position and the catheter tip decreases. Likewise, it may have more influence when the distance increases. The predetermined position may particularly be in the tubing system at a position which is closer to the catheter than to the pump, e.g. at a position with at least twice the distance to the pump compared to the distance to the catheter.

The measure of pressure allows the processor to determine or estimate a flow condition at the catheter tip. Particularly, determining a measure of pressure at a predetermined position in the tubing system and/or the catheter during operation of the pump, allows the processor to determine or estimate a flow condition at the catheter tip. For example, the rise of the pressure at a particular flow restrictor within the tubing system to a predetermined level may indicate the presence of irrigating liquid at the tip of the catheter. Similarly, the rise of pressure at the catheter tip itself may indicate the presence of irrigating liquid at the tip.

The control system may be configured for determining the flow condition before, during, and after anal or stoma irrigation. Particularly, the control system may be configured to determine presence of the irrigating liquid at the catheter tip and/or at the pump and/or at the aforementioned predetermined position or positions in the tubing system or catheter.

In one embodiment, the control system may comprise a memory for storing at least one pressure threshold value indicative of the presence of the irrigating liquid in at least the first predetermined position in the tubing system and/or the catheter and/or in at least one second predetermined position in the tubing system and/or the catheter. In such an embodiment, the control system may be configured to continue the pumping operation of the pump for a limited period of time after determination, by the at least one sensor, of a pressure value at the at least one first predetermined position which is at least equal to the pressure threshold value or a value derived therefrom. For example, one of the first and second predetermined positions may be a position at the catheter tip or in the vicinity thereof, in which case the control system may be configured to continue said pumping operation for a certain duration after the determination of said pressure threshold value. Accordingly, the amount of irrigating liquid expelled from the catheter tip may be accurately controlled by control of said duration.

The pressure sensors located at the mentioned predetermined locations could be pressure transducers working according to different sensing principles. As an example, a pressure sensor for use in accordance with the present invention may be a barometer, comprising a membrane which responds to a pressure change by displacing a needle; or a coil, which comprises a coiled tube that uncoils upon increasing pressure, thus displacing a needle. Typical materials for the pressure sensors in accordance with the present invention are plastic, metal, composite materials (e.g. fibreglass or carbon fibre materials).

The at least one pressure sensor may comprises a sensor arranged in the tubing system in the vicinity of the catheter or within the catheter itself, at any suitable position within the tubing and valve system.

It would be advantageous to measure pressure directly at the catheter tip. However, the catheter is typically a disposable component of anal or stomal irrigation systems, and space is limited.

When the system is primed, a vertical displacement of the catheter may cause a change in pressure due to gravity on the liquid column in the tubing system and catheter. In order to take into account the fact that the catheter tip, the reservoir and/or the pressure sensor may be at a different heights, the control system may be configured to determine a height difference between the catheter, reservoir and/or pressure sensor, and to correct the measure of pressure as determined by said sensor on the basis of said height difference, i.e. to compensate pressure output in dependence of gravity-induced pressure.

There are different ways of obtaining a measure of the height, e.g. by incorporating the one or more pressure sensors in the control unit, between the pump and the catheter tip, at least some of the effect of gravity-induced pressure can be compensated for.

In one embodiment, the control system is configured to compare the measure of pressure of a primed system with the measure of pressure of an empty system and use the comparison to determine the height of the catheter over the location where the pressure is measured. In another embodiment, different pressures at different locations are determined in order to estimate the height of the catheter relative to the other parts of the system.

With knowledge of:

The hydraulic properties from the control unit to the catheter tip (diameters, surfaces and lengths, turns)
The water flow (Q)
The height difference between CU and catheter tip (H)
The pressure at the control unit (Pcu)
It is possible to assess the pressure at the tip of the catheter (Ptip).
If the viscosity is considered relatively constant, the equation is:

$$Ptip=Pcu-Pdyn+/-Pstat$$

where:
Pdyn is a function of the constant and known hydraulic properties and the flow Q. If Q is "0", Pdyn is "0"
Pstat is maximally equivalent to the height difference between the control unit and the catheter tip. If H is "0" Pstat is "0". It may be plus or minus depending on whether the control unit is above or below the catheter tip.

The control system according to the invention may be configured to determine the pressure at the tip, Ptip, e.g. by use of the above expression.

Likewise, the control system may be configured to determine a dynamic pressure at the catheter and to correct the measure of pressure as determined by said sensor on the basis of the dynamic pressure.

The system may comprise a plurality of pressure sensors arranged at respective positions within the tubing system and/or the catheter, whereby the control system may be configured to control the pumping operation of the pump in response to the determination of a predetermined set of pressure values at said positions. Hence, for example, a pattern of pressure increases across multiple flow restrictors may be recognized by the control system and utilized to assess the position, within the tubing system, of a flow front of the irrigating liquid.

By combining the at least one sensor for determining an amount of current or power consumed by electric motor with at least one pressure sensor, it is possible to determine a fault in either one of these sensors and whether the tubing is obstructed (e.g. by a kink) between the motor and the pressure sensor. In one embodiment, the control system is configured to determine a malfunction by combining a measure of pressure at one location with a measure of pressure from another location.

With a view to reduce the risk of microbiological contamination at the catheter and the tubing system connecting to the catheter, notably with a view to limit or eliminate the risk of bacteria- or bio-film growth at the catheter and the collection of bacteria within the tubing system, the control system may be further configured to drive the pump in a non-irrigation mode following expelling of irrigating liquid in the irrigation mode, i.e. subsequently to irrigation of the user's rectum. Accordingly, the pumping operation of the pump may be continued so as to expel the irrigating liquid at a second flow rate in the non-irrigation operating mode. Preferably, the second flow rate is lower than a first flow rate used for irrigation. Thus, a relatively low rate of irrigating liquid flow may be expelled from the catheter tip subsequent to irrigation, thereby providing a moderate fluid flow in the conduits connecting to the catheter, so as to flush microorganisms away from the catheter and/or out of the tubing conduits. Hence, the risk of biological or bacterial contamination being collected at the catheter or within the tubing system may be reduced.

After flushing the catheter and tubing system with irrigating liquid, air is pumped through the catheter and tubing system. Irrigating liquid is thereby emptied from the catheter and tubing system, and the system is ready for storage and/or transport.

The system may comprise a valve system comprising at least a first valve arranged in the conduit between the pump and the catheter tip to control flow of irrigation liquid to the catheter tip. The first valve may thus prevent flow of the irrigation liquid when closed. The first valve may be electrically operable by use of the control system. Accordingly, the control system may be configured not only for controlling the pump but also for controlling the valve system, and it may thereby control the flow of liquid by use of the pump, the valve system or both the pump and valve system.

In embodiments, the catheter may comprise an expandable retention element for fixation of the catheter tip within the user's rectum or stoma. The conduit between the reservoir and the catheter tip may constitute a first conduit of the tubing system, and the tubing system may further comprise a second conduit between the reservoir and the expandable retention element.

The valve system may include a second valve in the second conduit for controlling the flow of the irrigating liquid between the reservoir and the expandable retention element, and the pump and the valve system may be controllable to selectively:
  pump the irrigating liquid into the expandable retention element for expansion thereof;
  pump the irrigating liquid through the catheter for expelling of the irrigating fluid from the catheter tip and into the user's rectum or stoma;
  withdraw the irrigating liquid from the retention element for purging thereof.

The ability of the pump and the valve system to withdraw the irrigating liquid from the retention element for purging thereof allows the retention element to be purged in a controlled manner. Expansion of the retention element as well as collapsing thereof may hence be accurately controlled by adequate control of the pump and the valve system. Collapsing of the retention element by a controlled action, notably by forced purging caused by a pumping action of the pump enables purging of the retention element even under circumstances, at which the retention element is expanded by a relatively low pressure, which is too low for the irrigating liquid to escape from the retention element merely be opening a valve of the valve system.

The control system may be configured to control at least one of the pump and the valves to provide a control sequence comprising a first state where both the first and the second valve are closed while the pump is operating, and a subsequent second state where at least one of the first and second valves is open while the pump is operating.

The shift from the first to the second state enables a more abrupt pressure control where the pressure shifts from low to high or from high to low in very short time. The pump may e.g. be operated until it reaches its max speed or to a predefined speed before one of the valves are opened. This makes the pressure control more precise.

The pump is suitably a rotary pump such as a gear pump, an impeller pump, or a screw pump. Such pumps can provide relatively accurately measured volumes of liquid, can operate in reverse, and usually allow a small amount of back-flow.

The valve system within the tubing system is preferably configured to selectively cause one flow configuration selected from a first, second and third flow configuration at a time, wherein:

the first flow configuration is arranged to cause a transfer of the irrigating liquid, by means of said pump, from the reservoir into the expandable retention element;

the second flow configuration is arranged to transfer the irrigating liquid, by means of said pump, from the reservoir to the catheter;

the third flow configuration is arranged to transfer the irrigating liquid, by means of said pump, away from the expandable retention element.

Thus, in the first flow configuration the irrigating liquid is transferred from the reservoir to the expandable retention element for expansion thereof. In the second flow configuration, the irrigating liquid is transferred from the reservoir to the catheter, i.e. to the catheter tip for insertion into the user's rectum or stoma. In the third flow configuration, the irrigating liquid is transferred away from the expandable retention element, either directly to the catheter tip for flushing of the user's bowel without the irrigating liquid passing into or through the reservoir, or back to the reservoir.

A thermosensor may further be provided, which is connected to the reservoir for obtaining a measure of a temperature within the reservoir, the tubing system and/or the catheter. The control system may be operatively connected with the thermosensor, and the control system may be configured to determine a temperature within the reservoir before the irrigating liquid is filled or re-filled into the reservoir, determine an initial change of the temperature within the reservoir upon commencement of filling or refilling of the irrigating liquid into the reservoir, and predict a future asymptotic value of the temperature within the reservoir on the basis of at least the initial change. The control system may further be configured to continuously determine a current temperature or a current rate of change of the temperature within the reservoir while the irrigating liquid is filled or refilled into the reservoir, and to continuously update the prediction of the future asymptotic value of the temperature within the reservoir on the basis of at least said current temperature and/or rate of change of the temperature.

Thanks to the thermosensor and the control system, a prediction of the future asymptotic value of the temperature within the reservoir once filled, notably of the irrigating liquid, may be made. As the prediction of the future asymptotic temperature value is continuously updated on the basis of the current temperature and/or the rate of change of temperature, a change of temperature of the liquid supplied to the reservoir, such as for example a change of the ratio between hot and cold tap water, is adequately reflected in the temperature prediction. The temperature prediction may be communicated to the user, e.g. via a display of the system, thus allowing the user to ascertain if the temperature of the supplied liquid, typically tap water, is to be increased or decreased.

BRIEF DESCRIPTION OF THE DRAWINGS

Embodiments will now be further described with reference to the accompanying drawings, in which.

DETAILED DESCRIPTION OF THE DRAWINGS

Figure 1:
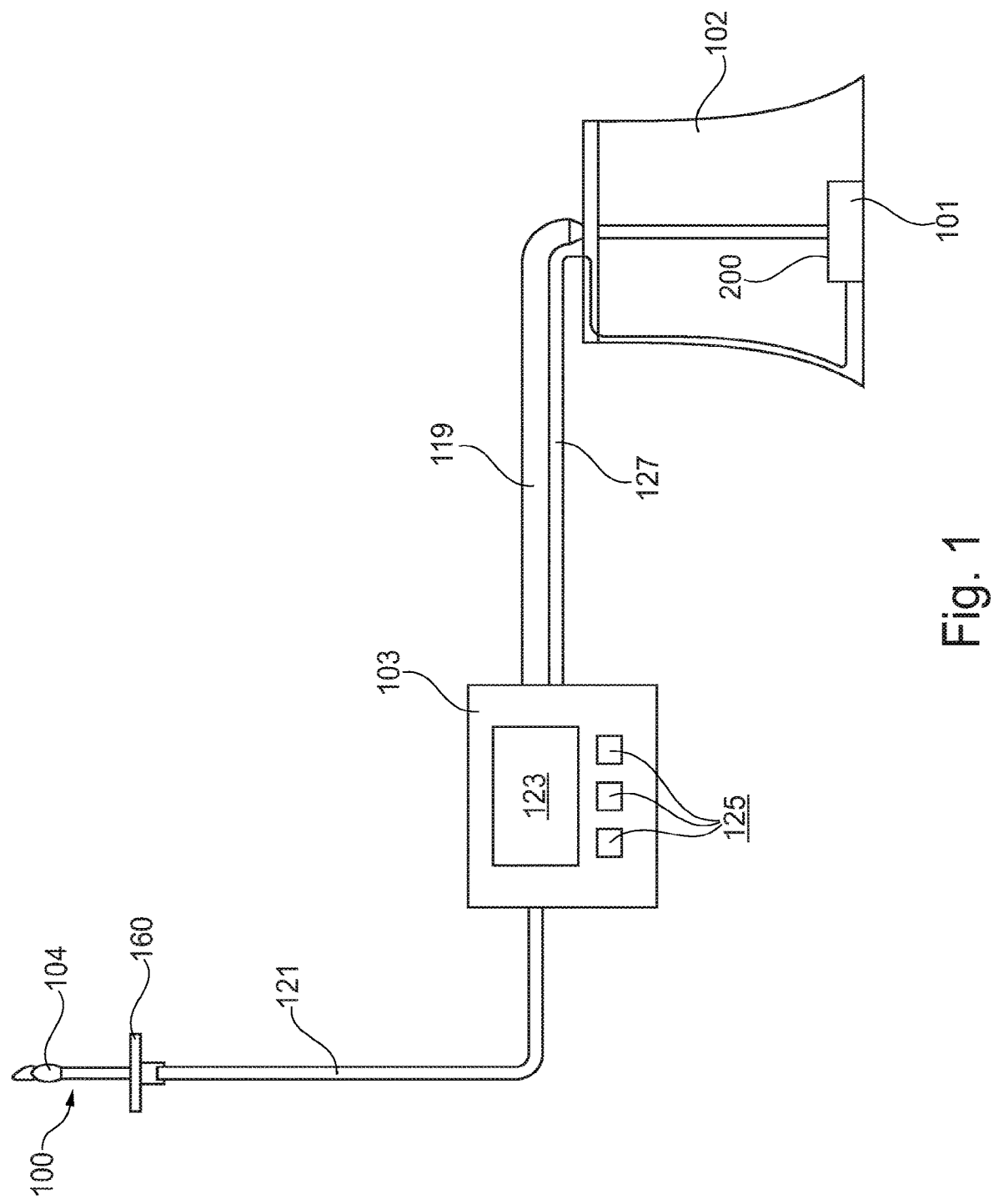
FIG. 1 shows an embodiment of a system for anal and/or stomal irrigation.

FIG. 1 shows an embodiment of a system for anal and/or stomal irrigation. The system comprises a catheter 100 sized and configured for insertion into the rectum or stoma of a user. A pump 101 is provided in a reservoir 102 for transferring an irrigating liquid contained within said reservoir 102 to the catheter 100 and to an expandable retention element 104 in the form of a balloon configured to fix the catheter within the user's rectum or stoma. Pump 101 is located within a housing 200.

The catheter 100 is typically a disposable component. To this effect, a coupling means 160 is located between the catheter 100 and tube portion 121. Coupling means 160 allows the catheter 100 to be disconnected from the tube portion 121, and replaced as required. The coupling means 160 may take the form of a bayonet coupling, a push-coupling or a screw coupling.

First tube portion 119 extends between the pump 101 and a control unit 103, while second tube portion 121 extends between the control unit 103 and the catheter 100 and expandable retention element 104. The control unit 103 for the pump 101 is thus located between the liquid reservoir 102 and the catheter 100, in a convenient position for a user.

First and second tube portions 119 and 121 include separate conduits for connecting the pump to the catheter for expelling of irrigating liquid from the catheter tip and for expansion of the balloon 104, respectively.

The control unit 103 is provided with a display 123 for communicating an operating state of the system and/or an asymptotic temperature value to the user, and user-operable control buttons 125 are provided as part of a user operable control interface for controlling operation of the pump 101. A wired connection 127 is provided for communicating a signal between the pump 101 and the control system 103.

Figure 2:
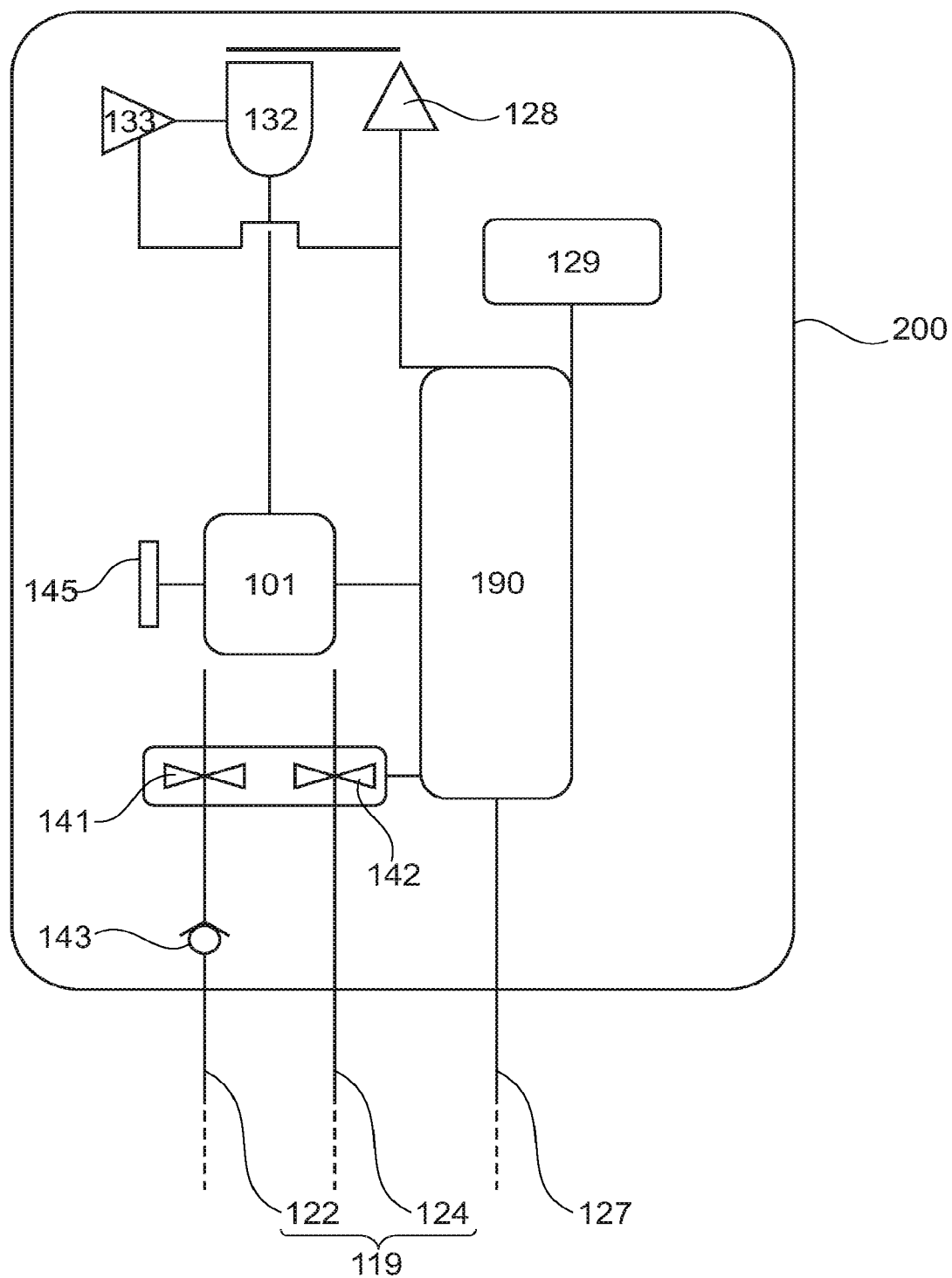
FIG. 2 shows an embodiment of the housing of the pump of the system according to FIG. 1.

FIG. 2 illustrates an embodiment of the housing 200 of the pump 101, according to FIG. 1. The illustrated housing 200 is liquid-tight, and comprises pump 101, thermosensor 128, battery 129, and charging port 130 for said battery 129. As shown in FIG. 2, a first electronic control board 190 is located in the housing 200, and links the pump 101, thermosensor 128 and battery 129. The first electronic control board 190 within housing 200 is connected to the control unit 103 (FIG. 1) via wired connection 127. The exact components of the housing 200 are not limited by this embodiment, and one or more of such components may be added, removed, or replaced by equivalent components, as deemed necessary by the skilled person.

The housing 200 comprises an inlet 132 which allows liquid to flow between the reservoir and the pump 101. Inlet 132 is controlled by inlet valve 133. The electronic control board 140 also controls inlet valve 133. The pump 101 is suitably a gear pump.

An irrigation conduit 122 is arranged to receive irrigating liquid from the pump 101 and transfer it to the catheter 100 for anal irrigation. An irrigation conduit valve 141 is located in said irrigation conduit 122, for controlling the liquid flow in this conduit. Irrigation conduit valve 141 is controlled by electronic control board 140.

A balloon conduit 124 is arranged to receive irrigating liquid from the pump 101 and transfer it to the expandable retention element 104. A balloon conduit valve 142 is located in said balloon conduit 124, for controlling the liquid flow in this conduit. Balloon conduit valve 142 is controlled by electronic control board 190.

Balloon conduit valve 142 and irrigation conduit valve 141 allow liquid to escape from the balloon 104 or from the catheter 100 in case the pressure therein exceeds the threshold pressure defined by these valves. Balloon conduit valve 142 drains liquid from the balloon 104 to the reservoir 102 in the case of excessive pressure within the balloon 104, and the irrigation conduit valve 141 drains liquid from the catheter 100 to the reservoir 102 in the case of excessive pressure within the user's rectum or stoma.

A check valve 143 is also located in the irrigation conduit 122. The check valve 143 acts to prevent backflow of irrigating liquid from the catheter 100, or any position downstream of the pump, to the reservoir 102.

Housing 200 also comprises an encoder 145, which converts digital signals from the first electronic control board 140 into control signals for the motors of pump 101.

Figure 3:
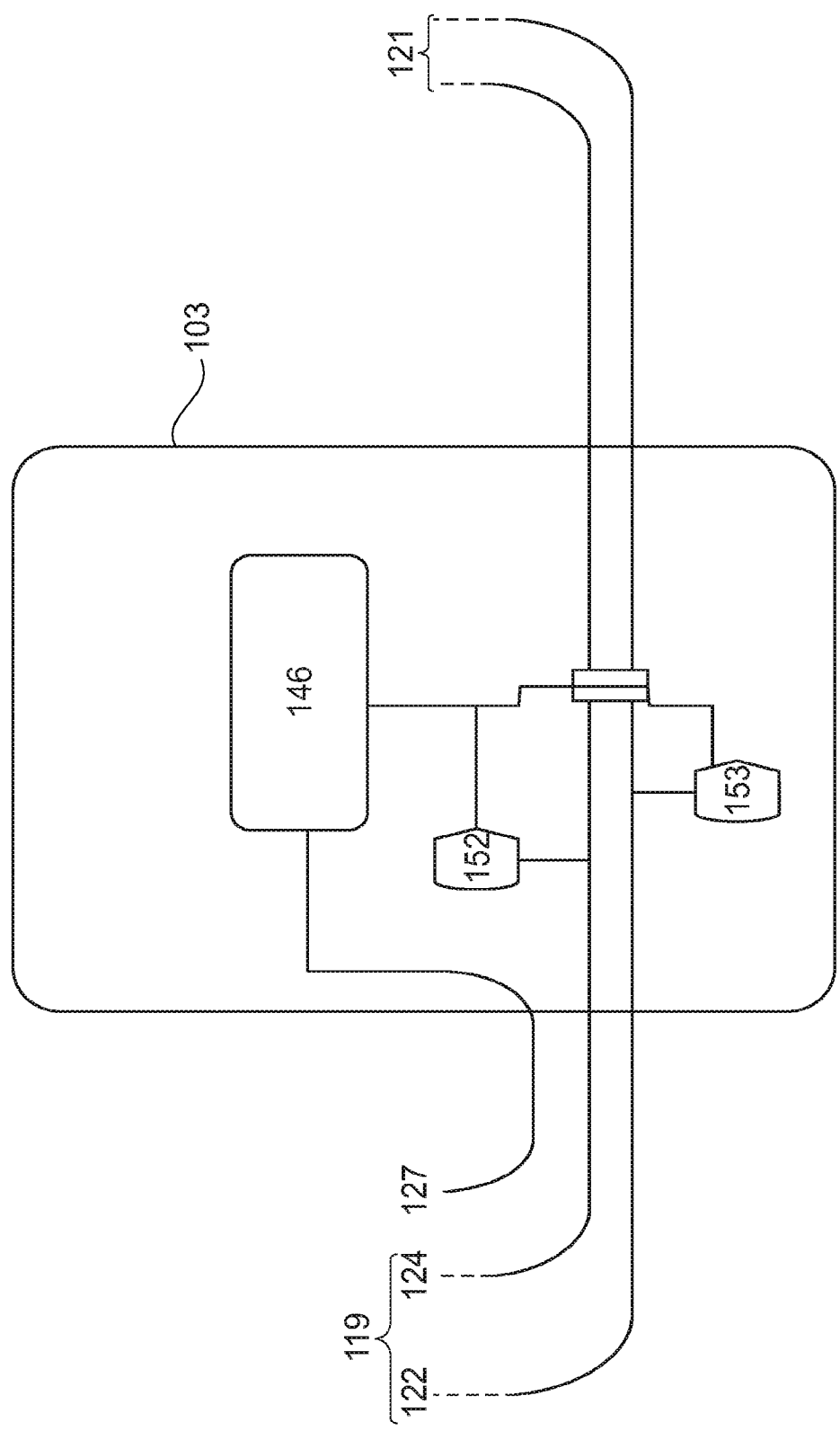
FIG. 3 shows an embodiment of the control unit of the system according to FIG. 1.

FIG. 3 illustrates the components of the control unit 103 shown in FIG. 1. As shown, the control unit comprises a second electronic control board 146, which is connected to the first electronic control board 190 in housing 200 (see FIG. 2) via wired connection 127.

The first tube portion 119, comprising conduits 124 and 122 extends from the pump housing 200 to the control unit 103, as does wired connection 127. Conduits 124 and 122 pass through the control unit to the catheter 100 and expandable retention element 104, via said second tube portion 121.

The exact components of the control unit 103 are not limited by this embodiment, and one or more of such components may be added, removed, or replaced by equivalent components, as deemed necessary by the skilled person.

The second electronic control board 146 receives input from a user, and thermosensor 128 (in pump housing 200, FIG. 2), and communicates data to a display. The data communicated to the display may include a predicted future asymptotic value of the temperature of the irrigating liquid within the reservoir 102 as determined by thermosensor 128. The data may be continuously updated as the second electronic control board 146 continuously updates the temperature prediction while irrigating liquid is being filled or re-filled into the reservoir.

Balloon pressure sensor 152 is located in the control system 103, and acts to measure the pressure in the balloon conduit 124. Irrigation pressure sensor 153 is located in the control system 103, and acts to measure the pressure in the irrigation conduit 122. Pressure sensors 152 and 153 are also connected to the second electronic control board 146 within the control unit 103. The pressure sensors 152, 153 output a signal to the control system 103, which operates the pump 101 and/or the actively controllable balloon conduit valve 142 and irrigation conduit valve 141, on the basis of said signal and other signals as described herein.

A control system comprises a controller for controlling operation of the pump; at least one sensor for determining a measure of pressure in the tubing system and/or the catheter during operation of the pump and a processor. First and second control boards 190, 146, either jointly or individually, comprise the processor of the control system. The control system may determine or estimate a flow condition at the catheter tip on the basis of the measure of pressure provided by pressure sensors 152, 153. The control system is configured to control the pumping operation of the pump 101 in response to said measure of pressure. More specifically, the control system continues pumping operation of the pump 101 for a limited period of time after determination, by the pressure sensors 152, 153, of a pressure value which is at least equal to a pressure threshold value or a value derived therefrom.

In particular, by using the signal from the irrigation pressure sensor 153 in this manner, the amount of irrigating liquid expelled from the catheter tip may be accurately controlled. As an alternative to the embodiment shown, the irrigation pressure sensor 153 may be arranged in the tubing system 121, 124 in the vicinity of the catheter 100 or within the catheter 100 itself.

In a first flow configuration, the balloon conduit valve 142 is open, and the irrigation conduit valve 141 is closed while the pump 101 operates. Accordingly, irrigating liquid is transferred from the reservoir 102 to the balloon 104 for expansion thereof.

In a second flow configuration, the irrigation conduit valve 141 is open, and balloon conduit valve 142 is closed while the pump 101 operates. Irrigating liquid is thus transferred from the reservoir 102 to the catheter 100, at the tip of which the liquid is expelled into the user's rectum or stoma so as to irrigate the user's bowel.

Figure 4:
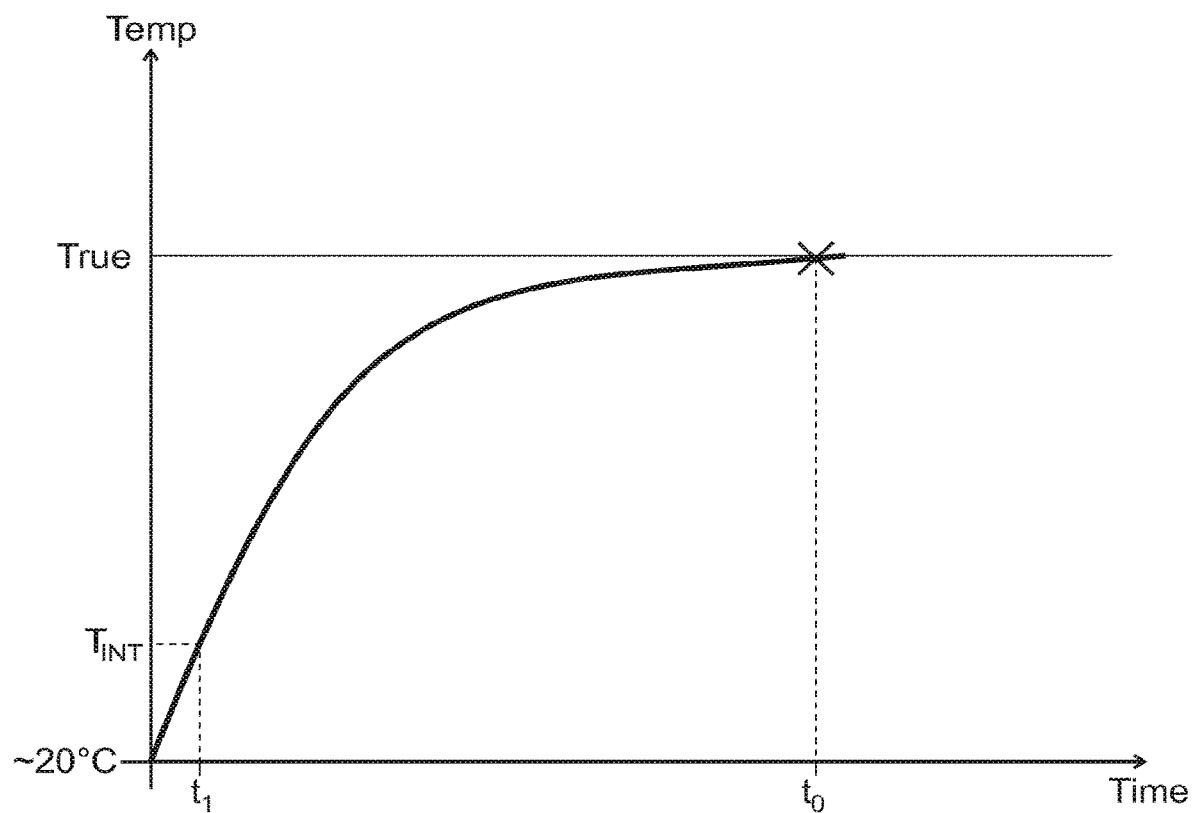
FIGS. 4 and 5 illustrate exemplary curves of temperature of an irrigating liquid in a reservoir during filling or refilling of irrigating liquid into the reservoir.
Figure 5:
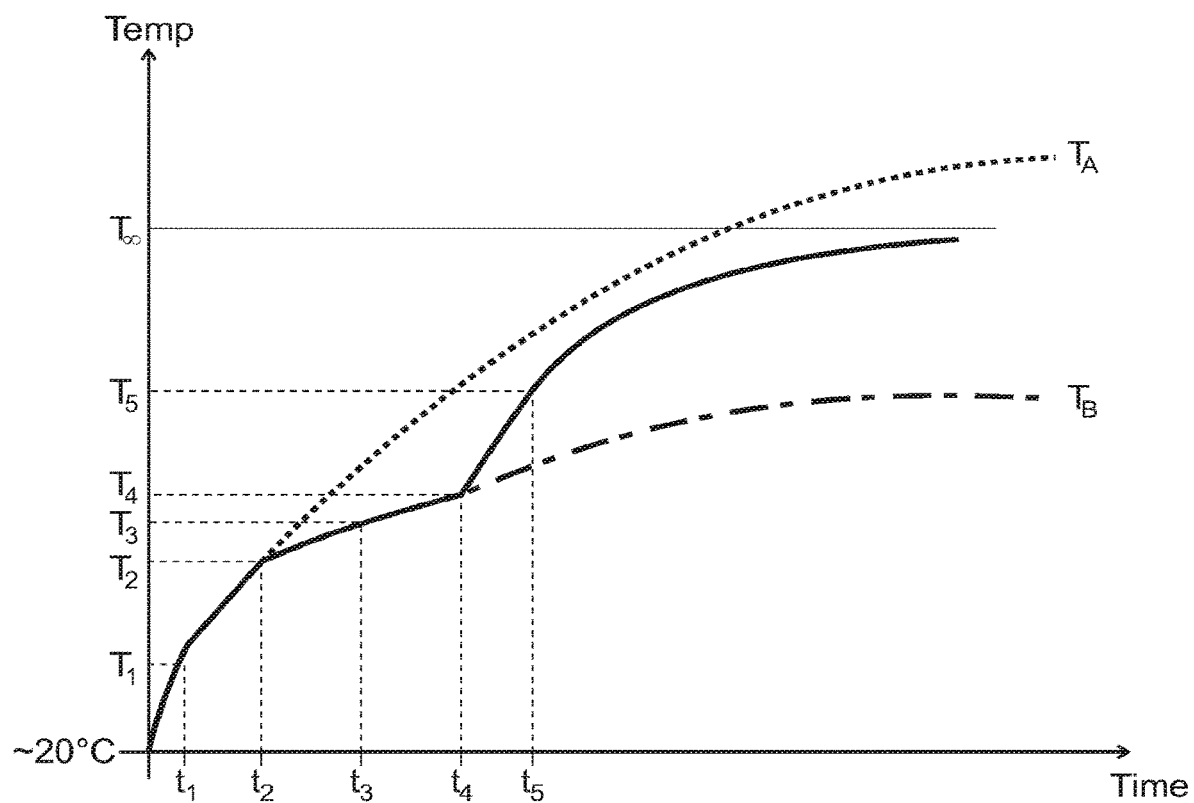

In a third flow configuration, operation of the pump 101 is reversed and balloon conduit valve 142, while the irrigation conduit valve 141 is closed. The balloon 104 is hence purged. FIGS. 4 and 5 illustrate exemplary curves of temperature of the irrigating liquid in the reservoir 102 during filling or refilling of irrigating liquid into the reservoir. In the chart of FIG. 4, the initial temperature of the irrigating liquid within the reservoir 102 as determined by thermosensor 128 is approximately 20° C. As the user's bowel should be irrigated with liquid at a temperature not exceeding approximately 40° C., preferably at a temperature of 20-40° C., most preferably at a temperature of 36-38° C., the user starts pouring liquid, such as tap water, at an elevated temperature into the reservoir.

The operation of the system illustrated in FIGS. 1-3 will now be described. An initial change of the temperature within the reservoir is determined by the thermosensor 128 upon commencement of filling or refilling of the irrigating liquid into the reservoir 120. In FIG. 4, the initial temperature change is represented by elevated temperature $T_{INT}$ at time $t_1$. On the basis of the initial temperature change, a future asymptotic value of the temperature, denoted "True" in FIG. 4, within the reservoir is predicted on the basis of at least the initial change.

As shown in FIG. 5, a current temperature or a current rate of change of the temperature within the reservoir is continuously determined by means of thermosensor 128 and control system 103, while the irrigating liquid is filled or refilled into the reservoir, and the prediction of the future asymptotic value of the temperature within the reservoir is continuously updated on the basis of at least said current temperature and/or rate of change of the temperature. More specifically, at the start of the filling or refiling procedure, an initial temperature change $T_1$ is determined at a first point in time, $t_1$. The first initial temperature change as represented by $T_1$ is used for a first prediction, $T_A$, of a future asymptotic temperature value of the irrigating liquid within the reservoir 102 once filled. At a second point in time, $t_2$, when the temperature as determined by the thermosensor 128 has reached level $T_2$, the temperature of the liquid supplied to the reservoir changes, for example as the user changes the ratio of hot to cold water in the tap. At a third point in time $t_3$, a third temperature value $T_3$ is obtained, and second prediction $T_B$ is made. Subsequently, at a fourth point in time, $t_4$, a fourth temperature level $T_4$ is reached, and the temperature of the liquid filled into the reservoir 102 changes abruptly for a second time. The change of the supplied liquid is reflected by temperature $T_5$ at time $t_5$, on the basis of which a third asymptotic temperature prediction $T_\infty$ is made.

During the above procedure, the predicted temperature values $T_A$, $T_B$ and $T_\infty$ are shown to the user via display 123 (see FIGS. 1 and 3) as they are determined by the control system 103.

Figure 6:
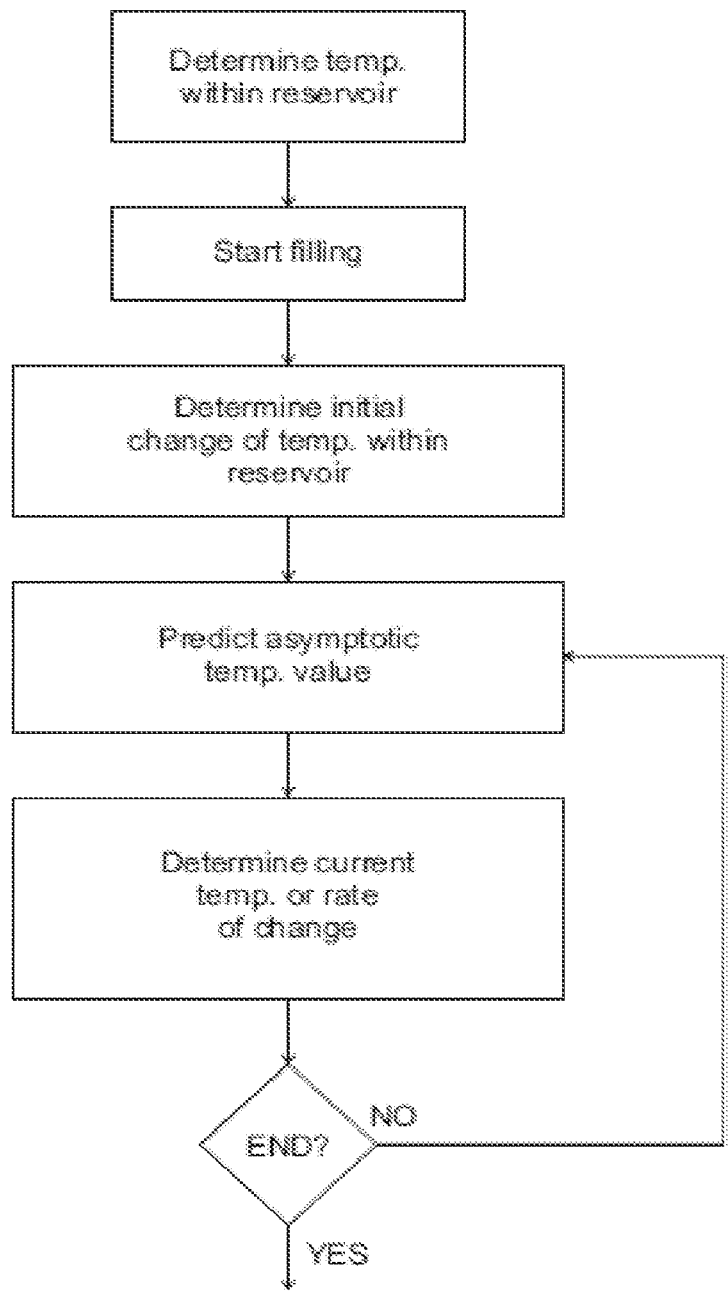
FIG. 6 illustrates an embodiment of a method for predicting a temperature of an irrigating liquid in a reservoir of a system for anal irrigation.

The above procedure of continuously determining and updating the asymptotic temperature prediction is generally depicted in FIG. 6.

Once the reservoir has been filled with the required volume of liquid, at the required temperature, the following steps are carried out:

i. The pump is operated with irrigation conduit valve and balloon conduit valve open. When liquid reaches the pump (indicated by an increase in the resistance in the pump operation), both these valves are closed.

ii. To prime the catheter, the irrigation conduit valve is opened sufficiently to fill the tubing, and the catheter packaging. This takes e.g. 30-40 ml of liquid, which can be correlated with a certain number of pump revolutions, or a certain time which the irrigation conduit valve is open. By filling the catheter packaging, a coating on the catheter is hydrated and made lubricious.

iii. Both irrigation conduit valve and balloon conduit valve are then closed, while the user inserts the catheter into the rectum.

iv. The user signals via the control unit that the catheter is in place. Filling of the balloon then begins.

v. To provide a more precise liquid flow, the pump is first operated (e.g. at 700-750 ml/minute) with both irrigation conduit valve and balloon conduit valve closed. At this point, any deviation from ideal pump operation can be detected by the first electronic control board (e.g. if too much current is drawn).

vi. The balloon conduit valve is then opened, so that irrigation liquid flows to the balloon and fills it. Again, the appropriate volume supplied to the balloon can be determined by a certain number of pump revolutions, or a certain time for which the balloon conduit valve is open.

vii. When the balloon is appropriately filled, the balloon conduit valve is closed. Pumping operation may be stopped.

viii. At this point, the static pressure (Pstat) in the balloon conduit can be measured by the balloon pressure sensor, and used to determine the height difference (H) between the control unit and the catheter tip. This height difference (H) can then be used to determine the static pressure Pstat in the irrigation conduit.

ix. Now, the balloon is full, the catheter is primed and a measure of Pstat in the irrigation conduit is known.

x. Pumping operation is started, while both irrigation conduit valve and balloon conduit valve are closed.

xi. The user signals the volume of liquid required for irrigation. This can be in the range 100-1000 ml, but is typically around 300-400 ml.

xii. The irrigation conduit valve is opened, and the required volume of irrigation liquid flows through the catheter and into the user's colon. As above, the required volume can be determined through a certain number of pump revolutions, or a certain time which the irrigation conduit valve is open.

xiii. A user can opt to introduce more liquid to the colon as required.

xiv. During irrigation operation, the control system constantly calculates the liquid pressure at the catheter tip (Ptip)—according to the formula given above—and regulates the pumping operation of the pump in response to Ptip.

xv. If the liquid pressure at the catheter tip (Ptip) approaches 2.0 psi, pump operation is slowed or stopped.

Figure 7:
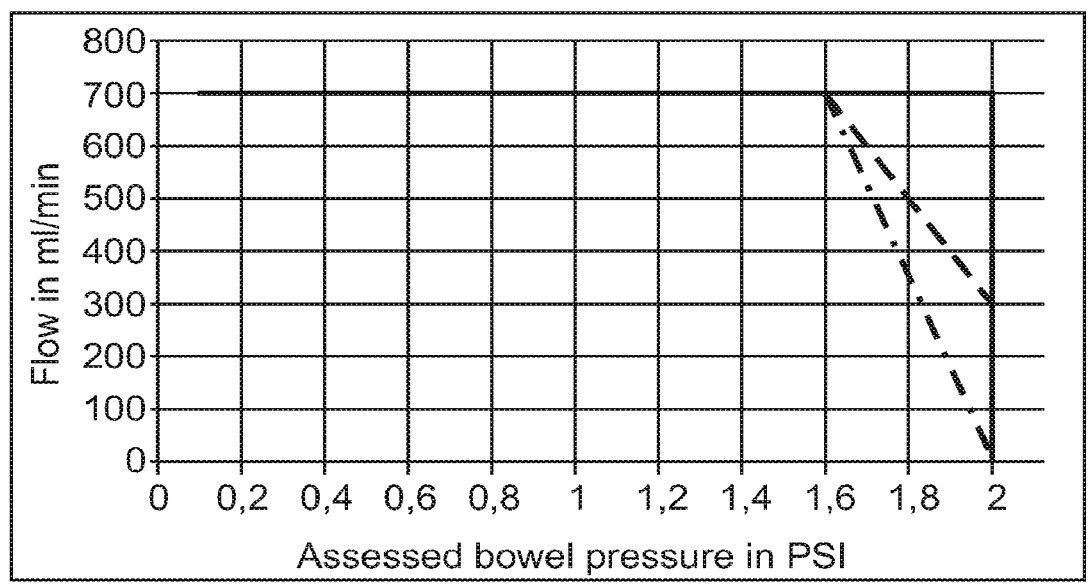
FIG. 7 illustrates exemplary curves of the flow of the irrigating liquid as a function of pressure, during operation of the system.

FIG. 7 illustrates an exemplary curve of the flow of the irrigating liquid as a function of pressure, during operation of the system. The user's bowel should be irrigated with liquid at a pressure not exceeding approximately 2 psi, preferably at a pressure of 1.5-1.9 psi, most preferably at a pressure of 1.6-1.7 psi.

In the chart of FIG. 7, the initial flow of the irrigating liquid as determined by the pump operating speed is approximately 700 ml/min. Accordingly, the assessed bowel pressure increases.

As the assessed bowel pressure approaches an intermediate value, e.g. between 1.4 and 1.6 psi, the liquid flow, as determined by the pump operating speed, is regulated by the control system, and falls gradually as the assessed bowel pressure nears a predetermined maximum value (in this case 2 psi).

The various plots in FIG. 7 illustrate how the liquid flow rate may be regulated as the bowel pressure approaches 2 psi. The solid line illustrates that liquid flow rate is held at a constant value of 700 ml/min until it is stopped at 2 psi. The dashed line illustrates that liquid flow rate begins to fall at around 1.6 psi, until 2 psi, where it is stopped. The line of alternating dashes and dots illustrates that the liquid flow rate begins to fall at around 1.6 psi and continues to fall until zero flow at 2 psi.

To remove the catheter from the rectum, the pump operates in reverse and the balloon conduit valve is opened, so as to empty liquid from the balloon.

Using "off-the shelf" components for a system, it has previously proven difficult to manufacture anal irrigation systems which meet the strict requirements for a maximum bowel pressure set out in the legislation (e.g. 2 psi). For instance, a difference in tubing diameter between two tubes, resulting from manufacturing tolerances, can lead to a difference in pressure between said tubes, when irrigation liquid is pumped through.

Accordingly, a method has been developed for calibrating a system as described herein. The method comprises the steps of:

providing an irrigation system according to the invention;

defining a predetermined height of the catheter tip above said reservoir, together with a corresponding pressure of the irrigating liquid at said predetermined height;

pumping irrigating liquid from the reservoir to the catheter tip;

measuring the pressure of the irrigating liquid at said predetermined position, by means of said at least one sensor; and determining or estimating the liquid pressure at the catheter tip on the basis of said measure of pressure at said predetermined position;

calibrating the system such that the determined or estimated pressure of the irrigating liquid at said catheter tip does not exceed 2 psi.

The step of calibrating the system may be carried out by e.g. limiting the pumping operation of the pump 101. For instance, the control system can be programmed such that a pump speed above a certain maximum value cannot be achieved. Alternatively, calibrating the system may be achieved by limiting the irrigation conduit valve 141 so that the determined or estimated pressure of the irrigating liquid at said catheter tip does not exceed 2 psi. Additionally or alternatively, a calibrating valve may be provided in the irrigation conduit 122 (e.g. within housing 200) which can be adjusted during manufacture of the system.

The predetermined height in the calibration method is typically the height of a toilet seat from the floor; e.g. 30-50 cm.

The following numbered aspects are provided:

Aspect 1. A system for anal and/or stomal irrigation comprising:
- a reservoir for an irrigating liquid;
- a catheter comprising a catheter tip for insertion into the rectum or stoma of a user and for expelling of the irrigating liquid from the catheter tip;
- a tubing system providing a conduit for the irrigating liquid between the reservoir and the catheter tip;
- a pump operable to pump the irrigating liquid from the reservoir to the catheter tip;
- a control system for controlling a flow condition of the irrigating liquid at the catheter tip during anal or stoma irrigation;

said control system comprising:
- a controller for controlling operation of the pump;
- at least one sensor for determining a measure of pressure at at least one first predetermined position in the tubing system and/or the catheter during operation of the pump;
- a processor for determining or estimating said flow condition at the catheter tip on the basis of said measure of pressure;

the control system being configured to control the pumping operation of the pump in response to said measure of pressure.

Aspect 2. The system as in Aspect 1, wherein the control system further comprises a memory for storing at least one pressure threshold value indicative of the presence of the irrigating liquid
- at at least the first predetermined position in the tubing system and/or the catheter and/or
- at at least one second predetermined position in the tubing system and/or the catheter; the control system being configured to continue the pumping operation of the pump for a limited period of time after determination, by the at least one sensor, of a pressure value at said at least one first predetermined position which is at least equal to the pressure threshold value or a value derived therefrom.

Aspect 3. The system as in Aspect 1 or 2, wherein said at least one sensor comprises at least one pressure sensor.

Aspect 4. The system as in any of the preceding Aspects, wherein the at least one pressure sensor comprises a sensor arranged in the tubing system in the vicinity of the catheter or within the catheter.

Aspect 5. The system as in Aspect 4, wherein the control system is configured to determine a height difference between a position of the catheter and a position of the reservoir and to correct the measure of pressure as determined by said sensor on the basis of said height difference.

Aspect 6. The system as in Aspect 4 or 5, wherein the control system is configured to determine a dynamic pressure at the catheter and to correct the measure of pressure as determined by said sensor on the basis of said dynamic pressure.

Aspect 7. The system as in any of Aspects 3-5, wherein the at least one pressure sensor comprises a plurality of pressure sensors arranged at respective positions within the tubing system and/or the catheter, and wherein the control system is configured to control the pumping operation of the pump in response to the determination of a predetermined set of pressure values at said positions.

Aspect 8. The system as in Aspect 1 or 2, wherein said pump is driven by an electric motor, and wherein said at least one sensor for determining a measure of pressure comprises at least sensor for determining an amount of current or power consumed by electric motor.

Aspect 9. The system as in Aspect 8, wherein the control system is configured to determine said amount of current or power consumed by the electric motor at a constant speed of the motor.

Aspect 10. The system as in any of the preceding Aspects, wherein the control system is further configured to:
- control pumping operation of the pump to expel the irrigating liquid at a first flow rate in an irrigation operating mode;
- enter a non-irrigation mode following expelling of irrigating liquid in the irrigation mode; and
- control pumping operation of the pump to expel the irrigating liquid at a second flow rate in the non-irrigation operating mode;

wherein the second flow rate is lower than the first flow rate.

Aspect 11. The system of any of the preceding Aspects, wherein
- the catheter comprises an expandable retention element for fixation of the catheter tip within the user's rectum or stoma;

said conduit between the reservoir and the catheter tip constitutes a first conduit of the tubing system; and wherein the tubing system further comprises a second conduit between the reservoir and the expandable retention element; the system further comprising:
- a valve system in the second conduit for controlling the flow of the irrigating liquid between the reservoir and the expandable retention element; wherein the pump and the valve system is controllable to selectively:
- pump the irrigating liquid into the expandable retention element for expansion thereof;
- pump the irrigating liquid through the catheter for expelling of the irrigating fluid from the catheter tip and into the user's rectum or stoma;
- withdraw the irrigating liquid from the retention element for purging thereof.

Aspect 12. A method for controlling a system for anal and/or stomal irrigation, said system comprising:
- a reservoir for an irrigating liquid;
- a catheter comprising a catheter tip for insertion into the rectum or stoma of a user and for expelling of the irrigating liquid from the catheter tip;
- a tubing system providing a conduit for the irrigating liquid between the reservoir and the catheter tip;
- a pump operable to pump the irrigating liquid from the reservoir to the catheter tip;
- at least one sensor for determining a measure of pressure at at least one first predetermined position in the tubing system and/or the catheter during operation of the pump;
- a control system for controlling a flow condition of the irrigating liquid at the catheter tip during anal or stoma irrigation and for controlling operation of the pump; said method comprising operating the control system to:

determine a measure of pressure at at least one first predetermined position in the tubing system and/or the catheter during operation of the pump;

determine or estimate said flow condition at the catheter tip on the basis of said measure of pressure;

control the pumping operation of the pump in response to said measure of pressure.

What is claimed is:

1. A method for anal or stomal irrigation, the method comprising:

providing an irrigation system to a user with the system comprising a reservoir adapted to contain an irrigating liquid, a catheter comprising a catheter tip sized for insertion into one of a rectum and a stoma of the user, a tubing system providing a conduit for the irrigating liquid between the reservoir and the catheter tip, a pump operable to pump the irrigating liquid from the reservoir to the catheter tip, a control system, and a sensor located in the tubing system;

instructing the user to operate the system to expel the irrigating liquid from the catheter tip; and controlling an irrigation pressure with the control system in response to input from the sensor such that a pressure at the catheter tip approaches a predetermined threshold pressure value without exceeding the predetermined pressure value.

2. The method of claim 1, further comprising:

enhancing an irrigation experience of the user by gradually decreasing the pressure at the catheter tip to avoid a cut-off of pumping operation.

3. The method of claim 1, measuring a pressure of the irrigating liquid in the conduit of the tubing system.

4. The method of claim 1, wherein the pump comprises a motor, the method comprising measuring the irrigation pressure with the control system by measuring a value of a power signal from the motor.

5. The method of claim 1, further comprising:

priming the irrigation system by removing air from the tubing system by moving the irrigating liquid out of the reservoir and into the tubing system.

6. The method of claim 1, further comprising:

measuring a volume of irrigating liquid that leaves the irrigation system through the catheter.

7. The method of claim 1, wherein the sensor is located in the tubing system adjacent to the catheter, and the input from the sensor comprises a measuring pressure of the irrigating liquid in the catheter.

8. The method of claim 1, wherein the control system comprises a plurality of sensors including the sensor located in the tubing system and a second sensor in the catheter, the method comprising controlling the irrigation pressure in response to input from the sensor and the second sensor.

9. The method of claim 1, further comprising:

a catheter sensor located in the catheter, the method comprising measuring the irrigation pressure at the catheter tip in response to input from the catheter sensor.

10. The method of claim 1, wherein the control system comprises a processor, the method comprising determining a flow condition at one of the catheter tip and the tubing system with the processor.

11. The method of claim 1, further comprising determining a presence of the irrigating liquid at the catheter tip.

12. The method of claim 1, further comprising determining a presence of the irrigating liquid at the pump.

13. The method of claim 1, further comprising determining a presence of the tubing system.

14. The method of claim 1, further comprising pumping the irrigating liquid through of the pump for a period of time after determining a presence of the irrigating liquid at one of the catheter tip and the pump.

15. The method of claim 1, further comprising measuring a height difference between two different positions of one of the catheter, the tubing system, and the reservoir with the control system, and adjusting an operating pressure of the pump based on the height difference.

16. The method of claim 1, further comprising measuring a height difference between two different positions of one of the catheter, the tubing system, and the reservoir with the control system based on one of a static pressure and a dynamic pressure of the irrigating liquid in the tubing system.

17. The method of claim 1, further comprising determining a dynamic pressure difference between a position of the sensor and the catheter tip and adjusting the irrigation pressure based on the dynamic pressure difference.

18. The method of claim 1, further comprising:

pumping the irrigating liquid through the system at a first flow rate in an irrigation operating mode;

entering a non-irrigation mode and pumping the irrigating liquid at a second flow rate in the non-irrigation mode, where the second flow rate is lower than the first flow rate.

19. The method of claim 1, wherein the catheter comprises an expandable retention element and the conduit includes a first conduit and a second conduit, with a first valve located in the first conduit and a second valve located in the second conduit, the method comprising:

pumping the irrigating liquid into the expandable retention element;

pumping the irrigating liquid through the catheter and out from the catheter tip; and moving the irrigating liquid out of the retention element.

20. The method of claim 1, further comprising:

calibrating the irrigation system through a series of steps including:

defining a predetermined height of the catheter tip above the reservoir and measuring a first pressure of the irrigating liquid at the predetermined height;

pumping the irrigating liquid from the reservoir to the catheter tip;

determining a liquid pressure at the catheter tip based on the measurement of the first pressure; and calibrating the irrigation system such that the determined liquid pressure at the catheter tip does not exceed 2 psi.

21. The method of claim 1, comprising controlling that the pressure at the catheter tip asymptotically approaches the predetermined threshold pressure value without exceeding the predetermined pressure value.

* * * * *